US012708656B2

(12) United States Patent
Wickline et al.

(10) Patent No.: US 12,708,656 B2
(45) **Date of Patent: *Aug. 18, 2026**

(54) PEPTIDE-POLYNUCLEOTIDE-HYALURONIC ACID NANOPARTICLES AND METHODS FOR POLYNUCLEOTIDE TRANSFECTION

(71) Applicants: University of South Florida, Tampa, FL (US); Washington University, St. Louis, MO (US)

(72) Inventors: Samuel A. Wickline, Temple Terrace, FL (US); Hua Pan, Tampa, FL (US); Christine Thien-Nga Pham, St. Louis, MO (US); Huimin Yan, St. Louis, MO (US)

(73) Assignees: University of South Florida, Tampa, FL (US); Washington University, St. Louis, MO (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/056,823

(22) Filed: Nov. 18, 2022

(65) Prior Publication Data

US 2023/0263855 A1 Aug. 24, 2023

Related U.S. Application Data

(63) Continuation of application No. 16/870,035, filed on May 8, 2020, now Pat. No. 11,529,388.

(60) Provisional application No. 62/845,974, filed on May 10, 2019.

(51) Int. Cl.

| | |
|---|---|
| ***A61K 47/64*** | (2017.01) |
| ***A61K 9/51*** | (2006.01) |
| ***A61K 31/7105*** | (2006.01) |
| ***A61K 38/16*** | (2006.01) |
| ***A61P 9/00*** | (2006.01) |
| ***A61P 19/02*** | (2006.01) |
| ***C12N 15/85*** | (2006.01) |

(52) U.S. Cl.

CPC ................ *A61K 38/16* (2013.01); *A61K 9/51* (2013.01); *A61K 31/7105* (2013.01); *A61K 47/64* (2017.08); *A61P 9/00* (2018.01); *A61P 19/02* (2018.01); *C12N 15/85* (2013.01)

(58) Field of Classification Search

CPC .......... A61K 38/16; A61K 47/64; A61K 9/51; A61K 31/7105; A61P 9/00; A61P 19/02; C12N 15/85

See application file for complete search history.

(56) References Cited

U.S. PATENT DOCUMENTS

| | | | | |
|---|---|---|---|---|
| 8,617,516 | B2 | 12/2013 | Wickline et al. | |
| 9,987,371 | B2 * | 6/2018 | Wickline ............ | A61K 31/713 |
| 10,758,627 | B2 * | 9/2020 | Wickline ................. | A61P 9/10 |
| 2011/0123438 | A1 | 5/2011 | Wickline et al. | |

FOREIGN PATENT DOCUMENTS

| | | | | |
|---|---|---|---|---|
| CA | 2989200 | | 1/2017 | |
| CN | 105018529 | A | 11/2015 | |
| EP | 3316893 | | 5/2018 | |
| EP | 2941273 | | 8/2018 | |
| JP | 2018520154 | | 7/2018 | |
| KR | 101579879 | B1 | 12/2015 | |
| WO | 2009151788 | | 12/2009 | |
| WO | WO-2014107596 | A1 * | 7/2014 | .......... A61K 31/713 |
| WO | 2017004512 | | 1/2017 | |

OTHER PUBLICATIONS

Yan et al (Pharmaceutics, 2020 Vol 12, published online Jan. 17, 2020, pp. 1-12, IDS ref). (Year: 2020).*

Qiao et al (ACS Appl Mater Interfaces 2018, vol. 10, pp. 4569-4581, IDS ref). (Year: 2018).*

Nisbet et al (Veterinary Science vol. 93 (2012) pp. 488-493, IDS ref). (Year: 2012).*

Ganesh et al (Biomaterials vol. 34 (published Feb. 11, 2013: pp. 3489-3502; IDS reference) (Year: 2013).*

Choi et al (Biomaterials vol. 35 (published May 20, 2014: pp. 7121-7132; IDS reference) (Year: 2014).*

Zhou et al (J Clin Invest 2014; vol. 124 No. 10: pp. 4363-4374; IDS reference) (Year: 2014).*

Yan et al (Nature: Scientific Reports vol. 9:No. 442: pp. 1-7; published online Jan. 24, 2019; IDS reference) (Year: 2019).*

Jia et al in "Turning Toxicants into Safe Therapeutic Drugs: Cytolytic Peptide-Photosensitizer Assemblies for Optimized In Vivo Delivery of Melittin" Adv Healthcare Mater 2018, 7, 1800380, pp. 1-11, IDS ref) (Year: 2018).*

The Peeler Dissertation Univ of Washington, 2019; IDS ref (2019) (Year: 2019).*

Allen, Kelli D., and Yvonne M. Golightly. "Epidemiology of osteoarthritis: state of the evidence." Current opinion in rheumatology 27.3 (2015): 276.

Altschul, Stephen F., et al. "Basic local alignment search tool." Journal of molecular biology 215.3 (1990): 403-410.

Altschul, Stephen F., et al. "Gapped BLAST and PSI-BLAST: a new generation of protein database search programs." Nucleic acids research 25.17 (1997): 3389-3402.

Beaucage, S. L., and M. H. Caruthers. "Deoxynucleoside phosphoramidites—a new class of key intermediates for deoxypolynucleotide synthesis." Tetrahedron Letters 22.20 (1981): 1859-1862.

Boshart, Michael, et al. "A very strong enhancer is located upstream of an immediate early gene of human cytomegalovirus." *cell* 41.2 (1985): 521-530.

Chevalier, X., et al. "Intraarticular injection of anakinra in osteoarthritis of the knee: a multicenter, randomized, double-blind, placebo-controlled study." Arthritis Care & Research 61.3 (2009): 344-352.

Choi, Kyung-mi, et al. "Tumor-specific delivery of siRNA using supramolecular assembly of hyaluronic acid nanoparticles and 2b RNA-binding protein/siRNA complexes." Biomaterials 35.25 (2014): 7121-7132.

(Continued)

*Primary Examiner* — Catherine S Hibbert

(74) *Attorney, Agent, or Firm* — Meunier Carlin & Curfman LLC

(57) ABSTRACT

The present disclosure relates to nanoparticles and methods for polynucleotide transfection.

14 Claims, 5 Drawing Sheets

Specification includes a Sequence Listing.

(56) References Cited

OTHER PUBLICATIONS

Chou, Szu-Ting, et al. "Enhanced silencing and stabilization of siRNA polyplexes by histidine-mediated hydrogen bonds." Biomaterials 35.2 (2014): 846-855.
Clevers, Hans, and Roel Nusse. "Wnt/β-catenin signaling and disease." Cell 149.6 (2012): 1192-1205.
Corr, Maripat. "Wnt-β-catenin signaling in the pathogenesis of osteoarthritis." Nature clinical practice Rheumatology 4.10 (2008): 550-556.
Deshmukh, Vishal, et al. "A small-molecule inhibitor of the Wnt pathway (SM04690) as a potential disease modifying agent for the treatment of osteoarthritis of the knee." Osteoarthritis and cartilage 26.1 (2018): 18-27.
Ellman, Michael B., et al. "Biological impact of the fibroblast growth factor family on articular cartilage and intervertebral disc homeostasis." Gene 420.1 (2008): 82-89.
Ganesh, Shanthi, et al. "Hyaluronic acid based self-assembling nanosystems for CD44 target mediated siRNA delivery to solid tumors." Biomaterials 34.13 (2013): 3489-3502.
Henikoff, Steven, and Jorja G. Henikoff. "Amino acid substitution matrices from protein blocks." Proceedings of the National Academy of Sciences 89.22 (1992): 10915-10919.
Hochberg MC, Guermazi A, Guehring H, Aydemir A, Wax S, Fleuranceau-Morel P, et al. Efficacy and Safety of Intra-Articular Sprifermin in Symptomatic Radiographic Knee Osteoarthritis: Results of the 2-Year Primary Analysis from a 5-Year Randomised, Placebo-Controlled, Phase II Study [abstract]. Arthritis Rheumatol 2017, 69 (suppl 10).
Hou, Kirk K., et al. "Mechanisms of nanoparticle-mediated siRNA transfection by melittin-derived peptides." ACS nano 7.10 (2013): 8605-8615.
Hou, Kirk K., et al. "Melittin derived peptides for nanoparticle based siRNA transfection." Biomaterials 34.12 (2013): 3110-3119.
Kaneda, Megan M., et al. "Mechanisms of nucleotide trafficking during siRNA delivery to endothelial cells using perfluorocarbon nanoemulsions." Biomaterials 31.11 (2010): 3079-3086.
Karlin, Samuel, and Stephen F. Altschul. "Applications and statistics for multiple high-scoring segments in molecular sequences." Proceedings of the National Academy of Sciences 90.12 (1993): 5873-5877.
Knudson, W., and R. F. Loeser. "CD44 and integrin matrix receptors participate in cartilage homeostasis." Cellular and Molecular Life Sciences CMLS 59.1 (2002): 36-44.
Kraus, V. B., et al. "Effects of intraarticular IL1-Ra for acute anterior cruciate ligament knee injury: a randomized controlled pilot trial (NCT00332254)." Osteoarthritis and cartilage 20.4 (2012): 271-278.
Lee, Min Sang, et al. "Target-specific delivery of siRNA by stabilized calcium phosphate nanoparticles using dopa-hyaluronic acid conjugate." Journal of Controlled Release 192 (2014): 122-130.
Li, Yanan, et al. "Co-delivery of siRNA and hypericin into cancer cells by hyaluronic acid modified PLGA-PEI nanoparticles." Drug development and industrial pharmacy 42.5 (2016): 737-746.
Lo, Grace H., et al. "Intra-articular hyaluronic acid in treatment of knee osteoarthritis: a meta-analysis." Jama 290.23 (2003): 3115-3121.
Luyten, Frank P., Przemko Tylzanowski, and Rik J. Lories. "Wnt signaling and osteoarthritis." Bone 44.4 (2009): 522-527.
Matteucci, Mark Douglas, and M. Ho Caruthers. "Synthesis of deoxyoligonucleotides on a polymer support." Journal of the American Chemical Society 103.11 (1981): 3185-3191.
Moore, E. E., et al. "Fibroblast growth factor-18 stimulates chondrogenesis and cartilage repair in a rat model of injury-induced osteoarthritis." Osteoarthritis and cartilage 13.7 (2005): 623-631.
Nalesso, Giovanna, et al. "WNT16 antagonises excessive canonical WNT activation and protects cartilage in osteoarthritis." Annals of the rheumatic diseases 76.1 (2017): 218-226.
Nalesso, Giovanna, et al. "WNT-3A modulates articular chondrocyte phenotype by activating both canonical and noncanonical pathways." Journal of Cell Biology 193.3 (2011): 551-564.
Newberry, Sydne J., et al. "Systematic review for effectiveness of hyaluronic acid in the treatment of severe degenerative joint disease (DJD) of the knee." (2015).
O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.
Olson, Steven A., et al. "Therapeutic opportunities to prevent post-traumatic arthritis: Lessons from the natural history of arthritis after articular fracture." Journal of Orthopaedic Research 33.9 (2015): 1266-1277.
Pan, Hua, et al. "Post-formulation peptide drug loading of nanostructures for metered control of NF-κB signaling." Biomaterials 32.1 (2011): 231-238.
Partlow, Kathryn C., Gregory M. Lanza, and Samuel A. Wickline. "Exploiting lipid raft transport with membrane targeted nanoparticles: a strategy for cytosolic drug delivery." Biomaterials 29.23 (2008): 3367-3375.
Rai, Muhammad Farooq, and Christine TN Pham. "Intra-articular drug delivery systems for joint diseases." Current opinion in pharmacology 40 (2018): 67-73.
Rai, Muhammad Farooq, et al. "Applications of RNA interference in the treatment of arthritis." Translational Research 214 (2019): 1-16.
Ran, Rui, et al. "Enhanced gene delivery efficiency of cationic liposomes coated with PEGylated hyaluronic acid for anti P-glycoprotein siRNA: A potential candidate for overcoming multi-drug resistance." International journal of pharmaceutics 477.1-2 (2014): 590-600.
Raviña, Manuela, et al. "Hyaluronic acid/chitosan-g-poly (ethylene glycol) nanoparticles for gene therapy: an application for pDNA and siRNA delivery." Pharmaceutical research 27.12 (2010): 2544-2555.
Setton, Lori. "Reservoir drugs." Nature materials 7.3 (2008): 172-174.
Shahin, Sophia A., et al. "Hyaluronic acid conjugated nanoparticle delivery of siRNA against TWIST reduces tumor burden and enhances sensitivity to cisplatin in ovarian cancer." Nanomedicine: Nanotechnology, Biology and Medicine 14.4 (2018): 1381-1394.
Shen, Yan, et al. "Co-delivery of siRNA and paclitaxel into cancer cells by hyaluronic acid modified redox-sensitive disulfide-crosslinked PLGA-PEI nanoparticles." Rsc Advances 5.58 (2015): 46464-46479.
Soman, Neelesh R., et al. "Molecularly targeted nanocarriers deliver the cytolytic peptide melittin specifically to tumor cells in mice, reducing tumor growth." The Journal of clinical investigation 119.9 (2009): 2830-2842.
Soman, Neelesh R., et al. "Synthesis and characterization of stable fluorocarbon nanostructures as drug delivery vehicles for cytolytic peptides." Nano letters 8.4 (2008): 1131-1136.
Taetz, Sebastian, et al. "Hyaluronic acid-modified DOTAP/DOPE liposomes for the targeted delivery of anti-telomerase siRNA to CD44-expressing lung cancer cells." Oligonucleotides 19.2 (2009): 103-116.
Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology 8.1 (1988): 466-472.
Van Amerongen, Renée. "Alternative Wnt pathways and receptors." Cold Spring Harbor perspectives in biology 4.10 (2012): a007914.
Waller, Kimberly A., et al. "Role of lubricin and boundary lubrication in the prevention of chondrocyte apoptosis." Proceedings of the National Academy of Sciences 110.15 (2013): 5852-5857.
Yan, Huimin, et al. "Development of a peptide-siRNA nanocomplex targeting Nf-κb for efficient cartilage delivery." Scientific reports 9.1 (2019), 442: 1-7.
Yan, Huimin, et al. "Suppression of NF-κB activity via nanoparticle-based siRNA delivery alters early cartilage responses to injury." Proceedings of the National Academy of Sciences 113.41 (2016): E6199-E6208.

(56) References Cited

OTHER PUBLICATIONS

Yang, Xiaoqian, et al. "Cluster of differentiation 44 targeted hyaluronic acid based nanoparticles for MDR1 siRNA delivery to overcome drug resistance in ovarian cancer." Pharmaceutical research 32.6 (2015): 2097-2109.

Yang, Xiaoqian, et al. "MDR1 siRNA loaded hyaluronic acid-based CD44 targeted nanoparticle systems circumvent paclitaxel resistance in ovarian cancer." Scientific reports 5 (2015): 8509.

Yuasa, Takahito, et al. "Wnt/β-catenin signaling stimulates matrix catabolic genes and activity in articular chondrocytes: its possible role in joint degeneration." Laboratory investigation 88.3 (2008): 264-274.

Zhdanov, Vladimir P. "Intracellular RNA delivery by lipid nanoparticles: Diffusion, degradation, and release." Biosystems 185 (2019): 104032.

Zhou, Hui-fang, et al. "Peptide-siRNA nanocomplexes targeting NF-κB subunit p65 suppress nascent experimental arthritis." The Journal of clinical investigation 124.10 (2014): 4363-4374.

Zhu, Mei, et al. "Activation of β-catenin signaling in articular chondrocytes leads to osteoarthritis-like phenotype in adult β-catenin conditional activation mice." Journal of Bone and Mineral Research 24.1 (2009): 12-21.

Qiao, Hongzhi, et al. "Nanostructured peptidotoxins as natural pro-oxidants induced cancer cell death via amplification of oxidative stress." ACS applied materials & interfaces 10.5 (2018): 4569-4581.

Jia, Hao-Ran, et al. "Turning toxicants into safe therapeutic drugs: cytolytic peptide—photosensitizer assemblies for optimized in vivo delivery of melittin." Advanced Healthcare Materials 7.16 (2018): 1800380.

Peeler Dissertation, 2019, Uni of Washington.

Yan, Huimin, et al. "Induction of WNT16 via peptide-mRNA nanoparticle-based delivery maintains cartilage homeostasis." Pharmaceutics 12.1 (2020): 73.

Nisbet, H. Ozlem, et al. "Evaluation of bee venom and hyaluronic acid in the intra-articular treatment of osteoarthritis in an experimental rabbit model." Research in Veterinary Science 93.1 (2012): 488-493.

Pham CT, Pan H and Wickline SA. Peptide-siRNA nanotherapeutics in arthritis. Oncotarget. 2015; 6:14731-2.

Lozhkin A, Vendrov AE, Pan H, Wickline SA, Madamanchi NR and Runge MS. Nadph oxidase 4 regulates vascular inflammation in aging and atherosclerosis. J Mol Cell Cardiol. 2017;102:10-21. 10.1016/j.yjmcc.2016.12.004.

Vendrov AE, Stevenson MD, Alahari S, Pan H, Wickline SA, Madamanchi NR and Runge MS. Attenuated Superoxide Dismutase 2 Activity Induces Atherosclerotic Plaque Instability During Aging in Hyperlipidemic Mice. Journal of the American Heart Association. 2017;6. 10.1161/JAHA.117.006775.

Pan H, Palekar RU, Hou KK, Bacon J, Yan H, Springer LE, Akk A, Yang L, Miller MJ, Pham CT, Schlesinger PH and Wickline SA. Anti-JNK2 peptide-siRNA nanostructures improve plaque endothelium and reduce thrombotic risk in atherosclerotic mice. Int J Nanomedicine. 2018; 13:5187-5205. 10.2147/IJN.S168556.

Kabir AU, Lee TJ, Pan H, Berry JC, Krchma K, Wu J, Liu F, Kang HK, Hinman K, Yang L, Hamilton S, Zhou Q, Veis DJ, Mecham RP, Wickline SA, Miller MJ and Choi K. Requisite endothelial reactivation and effective siRNA nanoparticle targeting of Etv2/Er71 in tumor angiogenesis. JCI Insight. 2018; 10.1172/jci.insight.97349.

Yan H, Duan X, Pan H, Akk A, Sandell LJ, Wickline SA, Rai MF and Pham CTN. Development of a peptide-siRNA nanocomplex targeting NF-kappaB for efficient cartilage delivery. Yan H, Duan X, Pan H, Akk A, Sandell LJ, Wickline SA, Rai MF and Pham CTN. Development of a peptide-siRNA nanocomplex targeting NF-kappaB for efficient cartilage delivery. Scientific Reports. 2019; 9:442.PMC6345850.

Mills KA, Quinn JM, Roach ST, Palisoul M, Nguyen M, Noia H, Guo L, Fazal J, Mutch DG, Wickline SA, Pan H and Fuh KC. p5RHH nanoparticle-mediated delivery of AXL siRNA inhibits metastasis of ovarian and uterine cancer cells in mouse xenografts. Scientific Reports. 2019; 9:4762.PMC6423014.

Strand MS, Krasnick BA, Pan H, Zhang X, Bi Y, Karnish C, Wetzel C, Sankpal N, Goedegebuure P, Fleming T, DeNardo DG, Gillanders WE, Hawkins WG, Wickline SA, Fields RC. Precision delivery of RAS-inhibiting siRNA to KRAS driven cancer via peptide-based nanoparticles. OncoTarget 2019; 10:4761-75. PMC6677667.

Lockhart J, VanWye J, Canfield J, Mong E, Wickline S, Pan H and Totary-Jain H. Systemic administration of selfassembled p5RHH-based nanoparticle delivers synthetic mRNA to plaques in a mouse model of atherosclerosis Biomaterials. 2019. 1744.

Zou W, Rohatgi N, Brestoff JR, Li Y, Williams JW, Pan H, Pietka TA, Newberry EP, Davidson NO, Dey A, Shoghi KI, Head RD, Wickline SA, Randolph GL, Abumrad NA and Teitelbaum SL. Deletion of ASXL2 in myeloid lineage cells prevents diet-induced obesity by maintaining energy expenditure. J Clin Invest. 2019.

MohanKumar K, Namachivayam K, Song T, Jake Cha B, Slate A, Hendrickson JE, Pan H, Wickline SA, Oh JY, Patel RP, He L, Torres BA and Maheshwari A. A murine neonatal model of necrotizing enterocolitis caused by anemia and red blood cell transfusions. Nat Commun. 2019;10:3494.PMC6677753.

Yan H, Hu Y, Akk A, Rai MR, Pan H, Wickline SA and Pham CTN. Induction of WNT16 via Peptide-mRNA Nanoparticle-Based Delivery Maintains Cartilage Homeostasis. Pharmaceutics. 2020. 73.

* cited by examiner

B

| Composition / Parameters | 1 µg WNT16 mRNA 10 µmol p5RHH | 2 µg WNT16 mRNA 10 µmol p5RHH | 4 µg WNT16 mRNA 10 µmol p5RHH |
|---|---|---|---|
| Average Size (nm) | 64.78 ± 8.344 | 105.5 ± 6.959 | 205.1 ± 6.109 |
| Zeta potential (mV) | -30.06 | -28.79 | -31.48 |

PEPTIDE-POLYNUCLEOTIDE-HYALURONIC ACID NANOPARTICLES AND METHODS FOR POLYNUCLEOTIDE TRANSFECTION

CROSS-REFERENCE TO RELATED APPLICATIONS

This application is a continuation application of U.S. patent application Ser. No. 16/870,035, filed on May 8, 2020, which claims priority to U.S. Provisional Application 62/845,974, filed on May 10, 2019, the entire contents of which are fully incorporated herein by reference.

STATEMENT REGARDING FEDERALLY SPONSORED RESEARCH

This invention was made with government support under Grant Nos. R01 DK102691 and R01 AR067491 awarded by the National Institutes of Health. The Government has certain rights in the invention.

SEQUENCE LISTING

A Sequence Listing conforming to the rules of WIPO Standard ST.26 is hereby incorporated by reference. Said Sequence Listing has been filed as an electronic document via Patent Center in ASCII format encoded as XML. The electronic document, created on May 16, 2023, is entitled "11001-048US2.xml", and is 8.812 bytes in size.

FIELD

The present disclosure relates to nanoparticles and methods for polynucleotide transfection.

BACKGROUND

Efficient and safe delivery of RNA is a key step for the application of RNA therapeutics. Despite promising data from ongoing clinical trials, the clinical use of RNA still requires the discovery and development of improved delivery systems. These new RNA carriers are needed in order to improve delivery efficiency and maximize therapeutic windows of RNA therapeutics in different human conditions with minimum toxicity.

RNA interference (RNAi) with the use of non-coding RNAs (for example, siRNA and miRNA) has been proposed as a highly specific and effective therapy for a number of diseases. However, despite nearly two decades of intense research since the discovery of RNAi, siRNA therapeutics have demonstrated limited success in translation to clinical applications due to poor cellular uptake and instability of free siRNA in serum. In addition, mRNA therapeutics have also seen increased interest for use as effective therapy for a number of diseases as well. What is needed are improved compositions for use in methods of delivering polynucleotides into cells and for use in improved therapeutic and pharmaceutical compositions.

The compositions and methods disclosed herein address these and other needs.

SUMMARY

Previous attempts to formulate peptide-polynucleotide nanoparticles yielded a mixture of particle sizes due to aggregation that could be controlled only partially by adding albumin to the particles after particle formation. Herein, the inventors unexpectedly found that the substitution of albumin with hyaluronic acid (HA) confers unexpected properties to the nanoparticles including a more uniform nanoparticle suspension. The novel hyaluronic acid nanoparticles also provide a surprisingly more potent effect than other nanoparticles, where 10-fold lower doses of siRNA were found to suppress aortic abdominal aneurysms. In addition, the novel hyaluronic acid nanoparticles can also complex with mRNA structures to form stable nanoparticles that are small enough to penetrate cartilage for delivery and translation of the mRNA.

In some aspects, disclosed herein is a pharmaceutical composition comprising a peptide-polynucleotide complex, the peptide-polynucleotide complex comprising: a peptide; a polynucleotide; and hyaluronic acid; wherein the peptide is non-lytic and capable of affecting the release of a polynucleotide from an endosome of a cell; and wherein the peptide comprises an amino acid sequence with at least 80% identity to the amino acid sequence of SEQ ID NO: 1 (VLTTGLPALISWIRRRHRRHC).

In some embodiments, the peptide-polynucleotide complex is about 10 nm to about 150 nm in diameter. In some embodiments, the peptide-polynucleotide complex is about 10 nm to about 50 nm in diameter. In some embodiments, the peptide-polynucleotide complex is about 20 nm to about 150 nm in diameter. In some embodiments, the peptide-polynucleotide complex is about 20 nm to about 40 nm in diameter.

In some embodiments, the hyaluronic acid coats the peptide-polynucleotide complex. In some embodiments, the hyaluronic acid is integrated into the peptide-polynucleotide complex.

In some embodiments, the polynucleotide is an RNA. In some embodiments, the polynucleotide is a non-coding RNA capable of regulating or inhibiting the expression of a nucleic acid sequence. In some embodiments, the non-coding RNA is an siRNA. In some embodiments, the non-coding RNA is an miRNA. In some embodiments, the polynucleotide is an mRNA.

In some embodiments, the peptide is cationic. In some embodiments, the peptide comprises an amino acid sequence with at least 85% identity to the amino acid sequence of SEQ ID NO: 1. In some embodiments, the peptide comprises an amino acid sequence with at least 90% identity to the amino acid sequence of SEQ ID NO: 1. In some embodiments, the peptide comprises an amino acid sequence with at least 95% identity to the amino acid sequence of SEQ ID NO: 1. In some embodiments, the peptide comprises SEQ ID NO: 1.

In some embodiments, the peptide consists of an amino acid sequence with at least 80% identity to the amino acid sequence of SEQ ID NO: 1. In some embodiments, the peptide consists of an amino acid sequence with at least 90% identity to the amino acid sequence of SEQ ID NO: 1. In some embodiments, the peptide consists of an amino acid sequence with at least 95% identity to the amino acid sequence of SEQ ID NO: 1. In some embodiments, the peptide consists of SEQ ID NO: 1.

In some embodiments, the peptide-polynucleotide complex comprises a ratio of peptide:polynucleotide that is more than about 50:1 and less than about 200:1.

In some aspects, disclosed herein is a method of delivering a polynucleotide to the cytoplasm of a cell, the method comprising: contacting a cell with a composition as described herein.

In some aspects, disclosed herein is a method of treating an inflammatory disorder in a subject, comprising administering to the subject a therapeutically effective amount of a composition as described herein.

In some aspects, disclosed herein is a method of treating osteoarthritis in a subject, comprising administering to the subject a therapeutically effective amount of a composition as described herein.

In some aspects, disclosed herein is a kit for preparing a peptide-polynucleotide complex, the kit comprising a first composition comprising a peptide, a second composition comprises a polynucleotide, and a third composition comprising hyaluronic acid (HA).

BRIEF DESCRIPTION OF THE DRAWINGS

The accompanying figures, which are incorporated in and constitute a part of this specification, illustrate several aspects described below.

FIG. 1A-1B show Atomic Force Microscopy images of hialuronan coated p5RHH-siRNA NP. Images were obtained by superimposing the amplitude and height layers in Adobe Photoshop. NP heights of are given by the scale to the right. FIG. 1C shows bright field images of NRK52E cells with superimposed Cy3 labeled (red) fluorescent NP indicating their intracellular uptake. FIG. 1D shows the same image as in (FIG. 1C) but superimposed Cy3 labeled fluorescent NP and DAPI (violet) fluorescence from NRK52E cells nuclei.

FIG. 2A is the plot that shows a 75% reduction in AAA incidence for p50 HA-NP compared to ineffective scrambled and naked NP (i.e., no enlargement in 75% of animals that do not exceed the red line for AAA) and significant mitigation of AAA, which is defined as an increase in aortic diameter (AD) of >100% at day 14 compared to pre-perfused AD on day 0. FIG. 2B shows immunofluorescence confocal micrographs show colocalization of p50-siRNA (Cy3-NP: red) and macrophages (MOMA-2: green) as an orange color, indicating uptake by inflammatory cells in the adventitia that are responsible for aneurysm enlargement. Nucleus is stained with DAPI. This aneurysm suppressing dose of siRNA is 10-fold less than that used for experiments with other nanoparticles, indicating that the HA coating unexpectedly confers much greater efficacy to the system for gene expression knockdown and/or protein knockdown.

FIG. 3A shows the size of NP was assessed by TEM and calculated according to the formula detailed in Materials and Methods section. Scale bar=100 μm. FIG. 3B shows characteristics of NP at different concentrations of mRNA. Size=mean±SE.

FIG. 4B shows quantitative eGFP by fluorescent intensity. DAPI stains nuclei. N=3 cartilage discs per treatment. Scale bar=25 um. ***P<0.001.

DETAILED DESCRIPTION

Figures 1A, 1B, 1C, 1D:
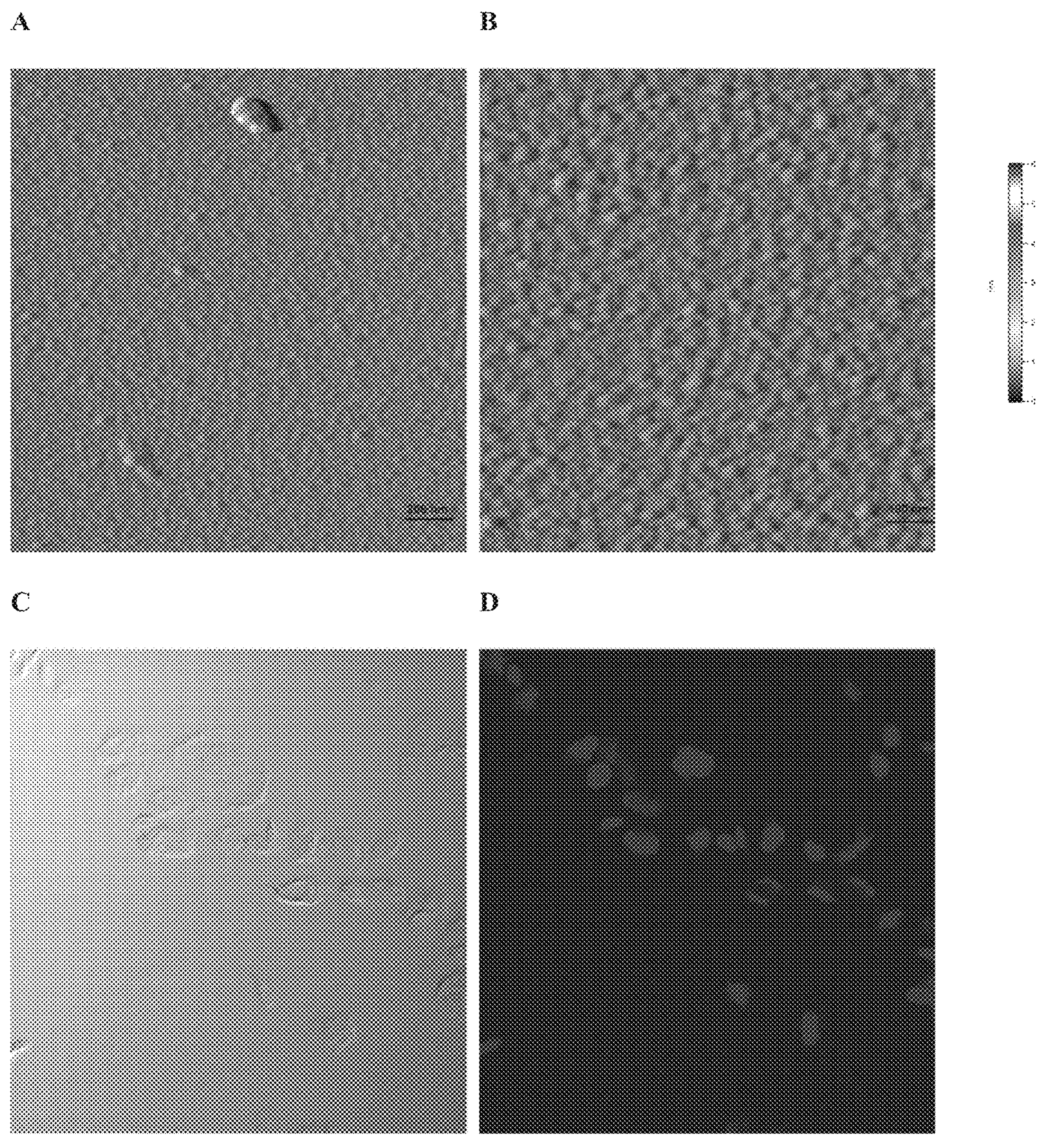
FIGS. 1A-1D illustrate hyaluronic acid (hialuronan) coated p5RHH-siRNA nanoparticle (NP) morphology and transfection.

Previous attempts to formulate peptide-polynucleotide nanoparticles yielded a mixture of particle sizes due to aggregation that could be controlled only partially by adding albumin to the particles after particle formation. Herein, the inventors unexpectedly found that the substitution of albumin with hyaluronic acid (HA) confers unexpected properties to the nanoparticles including a more uniform nanoparticle suspension. The novel hyaluronic acid nanoparticles also provide a surprisingly more potent effect than other nanoparticles where 10-fold lower doses of siRNA were found to suppress aortic abdominal aneurysms. In addition, the novel hyaluronic acid nanoparticles can also complex with mRNA structures to form stable nanoparticles that are small enough to penetrate cartilage for delivery and translation of the mRNA.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

The following definitions are provided for the full understanding of terms used in this specification.

Terminology

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed herein.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers.

The term "polypeptide" refers to a compound made up of a single chain of D- or L-amino acids or a mixture of D- and L-amino acids joined by peptide bonds. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr. Y), and valine (Val, V). The terms "polypeptide sequence" or "amino acid sequence" are an alphabetical representation of a polypeptide molecule.

Conservative substitutions of amino acids in proteins and polypeptides are known in the art. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

Substantial changes in protein function or immunological identity are made by selecting substitutions that are less conservative, i.e., selecting residues that differ more significantly in their effect on maintaining (a) the structure of the polypeptide backbone in the area of the substitution, for example as a sheet or helical conformation. (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

A "variant" refers to a molecule substantially similar in structure. Thus, in one embodiment, a variant refers to a protein whose amino acid sequence is similar to a reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 60%, 70%, 75%, 80%, 85%, 90%, or 95% identical to the reference sequence. For example, variant sequences which are at least 95% identical have no more than 5 alterations, i.e. any combination of deletions, insertions or substitutions, per 100 amino acids of the reference sequence.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8 (1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

As used herein, the phrase "functions substantially similar to a peptide comprising SEQ ID NO: X" refers to a substantially non-lytic and/or non-cytotoxic peptide that is capable of affecting the release of a polynucleotide from an endosome.

The term "non-lytic" means that the lipid bilayer of a cell typically is not compromised upon contact with the peptide. The integrity of the lipid bilayer may be assessed by the improper entry or exit of cellular or extracellular components into a cell. For example, cellular proteins and/or organelles may leak out of a cell with a compromised lipid bilayer. Alternatively, extracellular components (i.e., those that normally do not enter via gap junctions, for example) may enter a cell with a compromised lipid bilayer. It should be noted, however, that the peptide may penetrate the lipid bilayer of a cell and enter the interior of the cell, but in doing so the integrity of the lipid bilayer is not affected.

The term "non-cytotoxic" indicates that the cell typically is not killed upon contact with the peptide.

As used herein, the term "coat" or "coating" may refer to the interaction of a nanoparticle (peptide-polynucleotide complex) with a compound through non-covalent bonds, or to the covalent bonding of a nanoparticle and a compound.

The term "about" as used herein when referring to a measurable value such as an amount, a percentage, and the like, is meant to encompass variations of +20%, +10%, +5%, or +1% from the measurable value.

"Therapeutically effective amount" refers to the amount of a composition that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years. The therapeutically effective amount will vary depending on the composition, the disorder or conditions and its severity, the route of administration, time of administration, rate of excretion, drug combination, judgment of the treating physician, dosage form, and the age, weight, general health, sex and/or diet of the subject to be treated. The therapeutically effective amount as described herein can be determined by one of ordinary skill in the art.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. It will be understood, that the total daily usage of the compositions and formulations as disclosed herein will be decided by the attending physician within the scope of sound medical judgment. The exact amount required will vary depending on factors such as the type of disease being treated.

The terms "treat." "treating." "treatment," and grammatical variations thereof as used herein, include partially or completely delaying, alleviating, mitigating or reducing the intensity of one or more attendant symptoms of a disease. Treatments according to the invention may be applied preventively, prophylactically, palliatively or remedially. Prophylactic treatments are administered to a subject prior to disease onset. Prophylactic administration can occur for several minutes to months prior to the manifestation of disease.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

Compositions and Methods of Use

In some aspects, disclosed herein is a composition comprising a peptide-polynucleotide complex, the peptide-polynucleotide complex comprising:

a peptide;

a polynucleotide; and hyaluronic acid;

wherein the peptide is non-lytic and capable of affecting the release of a polynucleotide from an endosome of a cell; and wherein the peptide comprises an amino acid sequence with at least 80% identity to the amino acid sequence of SEQ ID NO: 1 (VLTTGLPALISWIRRRHRRHC).

In some embodiments, the peptide-polynucleotide complex is about 1 nm to 1000 nm in diameter. In some embodiments, the peptide-polynucleotide complex is about 10 nm to 500 nm in diameter. In some embodiments, the peptide-polynucleotide complex is about 10 nm to 300 nm in diameter. In some embodiments, the peptide-polynucleotide complex is about 200 nm to 300 nm in diameter. In some embodiments, the peptide-polynucleotide complex is about 200 nm to 280 nm in diameter. In some embodiments, the peptide-polynucleotide complex is about 200 nm to 260 nm in diameter. In some embodiments, the peptide-polynucleotide complex is about 200 nm to 240 nm in diameter. In some embodiments, the peptide-polynucleotide complex is about 200 nm to 220 nm in diameter. In some embodiments, the peptide-polynucleotide complex is about 190 nm to 210 nm in diameter. In some embodiments, the peptide-polynucleotide complex is about 180 nm to 200 nm in diameter. In some embodiments, the peptide-polynucleotide complex is about 170 nm to 190 nm in diameter. In some embodiments, the peptide-polynucleotide complex is about 160 nm to 180 nm in diameter. In some embodiments, the peptide-polynucleotide complex is about 150 nm to 170 nm in diameter. In some embodiments, the peptide-polynucleotide complex is about 140 nm to 160 nm in diameter. In some embodiments, the peptide-polynucleotide complex is about 130 nm to 150 nm in diameter. In some embodiments, the peptide-polynucleotide complex is about 120 nm to 140 nm in diameter. In some embodiments, the peptide-polynucleotide complex is about 110 nm to 130 nm in diameter. In some embodiments, the peptide-polynucleotide complex is about 100 nm to 120 nm in diameter. In some embodiments, the peptide-polynucleotide complex is about 90 nm to 110 nm in diameter. In some embodiments, the peptide-polynucleotide complex is about 80 nm to 100 nm in diameter. In some embodiments, the peptide-polynucleotide complex is about 70 nm to 90 nm in diameter. In some embodiments, the peptide-polynucleotide complex is about 60 nm to 80 nm in diameter. In some embodiments, the peptide-polynucleotide complex is about 50 nm to 70 nm in diameter. In some embodiments, the peptide-polynucleotide complex is about 40 nm to 60 nm in diameter. In some embodiments, the peptide-polynucleotide complex is about 10 nm to about 150 nm in diameter. In some embodiments, the peptide-polynucleotide complex is about 10 nm to about 50 nm in diameter. In some embodiments, the peptide-polynucleotide complex is about 20 nm to about 150 nm in diameter. In some embodiments, the peptide-polynucleotide complex is about 20 nm to about 40 nm in diameter.

In some embodiments, the peptide-polynucleotide complex is about 5 nm to about 50 nm in diameter. In some embodiments, the peptide-polynucleotide complex is about 10 nm to about 50 nm in diameter. In some embodiments, the peptide-polynucleotide complex is about 15 nm to about 45 nm in diameter. In some embodiments, the peptide-polynucleotide complex is about 20 nm to about 40 nm in diameter. In some embodiments, the peptide-polynucleotide complex is about 25 nm to about 35 nm in diameter. In some embodiments, the peptide-polynucleotide complex is about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm or more in diameter. In some embodiment, peptide-polynucleotide complex is smaller than about 160 nm in diameter. In some embodiment, peptide-polynucleotide complex is smaller than about 150 nm in diameter. In some embodiment, peptide-polynucleotide complex is smaller than about 140 nm in diameter. In some embodiment, peptide-polynucleotide complex is smaller than about 130 nm in diameter. In some embodiment, peptide-polynucleotide complex is smaller than about 120 nm in diameter. In some embodiment, peptide-polynucleotide complex is smaller than about 110 nm in diameter. In some embodiment, peptide-polynucleotide complex is smaller than about 100 nm in diameter. Particle size may be assessed using methods known in the art. Non-limiting examples of methods of measuring the size of a particle may include transmission electron microscopy (TEM), dynamic light scattering (DLS), laser diffraction, electrozone, light obscuration, sieve analysis, aerodynamic measurements, air permeability diameter, sedimentation, measuring the zeta potential of the particle, or combinations thereof.

In some embodiments, the hyaluronic acid coats the peptide-polynucleotide complex. In some embodiments, the hyaluronic acid is integrated into the peptide-polynucleotide complex.

In some embodiments, the polynucleotide is an RNA. In some embodiments, the polynucleotide is a non-coding RNA capable of regulating or inhibiting the expression of a nucleic acid sequence. In some embodiments, the non-coding RNA is an siRNA. In some embodiments, the non-coding RNA is an miRNA. In some embodiments, the polynucleotide is an mRNA.

A polynucleotide may be single stranded, double stranded, or a combination thereof. In some embodiments, a polynucleotide is double stranded. In other embodiments, a polynucleotide is single stranded. In yet other embodiments, a polynucleotide is a combination of single stranded and double stranded.

A polynucleotide may comprise a ribonucleic acid (RNA), a deoxyribonucleic acid (DNA), or a combination of RNA and DNA. Additionally, a polynucleotide may comprise modified nucleic acid bases, such as modified DNA bases or modified RNA bases. Modifications may occur at, but are not restricted to, the sugar 2' position, the C-5 position of pyrimidines, and the 8-position of purines.

Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). Alternatively, a polynucleotide may be a nucleotide mimic. Examples of nucleotide mimics include locked nucleic acids (LNA), peptide nucleic acids (PNA), and phosphorodiamidate morpholino oligomers (PMO).

In some embodiments, the polynucleotide comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the at least one chemically modified nucleotide is a chemically modified ribose. In some embodiments, the chemically modified ribose is 2'-O-methyl (2'-O-Me or 2'MeO or 2'-MeO) or 2'-fluoro (2'-F). In some embodiments, the chemically modified ribose is 2'-O-methyl (2'MeO). In some embodiments, the chemically modified ribose is 2'-fluoro (2'-F).

In some embodiments, the at least one chemically modified nucleotide is a chemically modified phosphodiester linkage. In some embodiments, the chemically modified phosphodiester linkage is phosphorothioate (PS). In some embodiments, all the nucleotides comprise chemically modified phosphodiester linkages.

In some embodiments, the polynucleotide is an RNA. In some embodiments, the polynucleotide is a non-coding RNA capable of regulating or inhibiting the expression of a nucleic acid sequence. In some embodiments, the non-coding RNA is an siRNA. In some embodiments, the non-coding RNA is an miRNA.

Non-limiting examples of non-coding RNA capable of regulating or inhibiting the expression of a nucleic acid sequence expressed in a cell include microRNAs (also known as miRNAs), siRNAs, piRNAs, shRNAs, and lncRNAs. In general, transfection of a cell with a non-coding RNA capable of regulating or inhibiting the expression of a nucleic acid sequence may lead to cleavage of the nucleic acid sequence, may enhance, prevent, or disrupt translation of the nucleic acid sequence into a protein, or may regulate the transcription of a nucleic acid sequence. In some embodiments, a polynucleotide of the invention comprises a non-coding RNA capable of disrupting expression of a nucleic acid sequence expressed in a cell. As used herein, "disrupting expression of a nucleic acid sequence" may be used to describe any decrease in the expression level of a nucleic acid sequence, or a protein translated from the nucleic acid sequence, when compared to a level of expression of the nucleic acid sequence in a cell that was not treated with a composition of the invention.

In some embodiments, the peptide comprises SEQ ID NO: 1. In some embodiments, the peptide consists of SEQ ID NO: 1. In some embodiments, the peptide comprises an amino acid sequence with at least 80% identity to the amino acid sequence of SEQ ID NO: 1.

In some embodiments, the peptide comprises an amino acid sequence with at least 85% identity to the amino acid sequence of SEQ ID NO: 1. In some embodiments, the peptide comprises an amino acid sequence with at least 90% identity to the amino acid sequence of SEQ ID NO: 1. In some embodiments, the peptide comprises an amino acid sequence with at least 95% identity to the amino acid sequence of SEQ ID NO: 1. In some embodiments, the peptide comprises SEQ ID NO: 1.

In some embodiments, the peptide consists of an amino acid sequence with at least 80% identity to the amino acid sequence of SEQ ID NO: 1. In some embodiments, the peptide consists of an amino acid sequence with at least 90% identity to the amino acid sequence of SEQ ID NO: 1. In some embodiments, the peptide consists of an amino acid sequence with at least 95% identity to the amino acid sequence of SEQ ID NO: 1. In some embodiments, the peptide consists of SEQ ID NO: 1.

In other embodiments, a peptide of the invention is substantially non-lytic. In other embodiments, a peptide of the invention is substantially non-cytotoxic. Typically, the peptide decreases cell viability by no more than about 10%, no more than about 7%, no more than about 5%, or no more than about 3%.

In some embodiments, the peptide is cationic. In some embodiments, the peptide comprises at least one hydrophobic segment. In some embodiments, the peptide further comprises at least one hydrophilic segment.

In some embodiments, the peptide comprises a variant of SEQ ID NO: 1, wherein the variant comprises at least 10 contiguous amino acids of SEQ ID NO: 1. In some embodiments, the peptide comprises a variant of SEQ ID NO: 1, wherein the variant comprises at least 10 contiguous amino acids of SEQ ID NO: 1 and functions substantially similar to a peptide comprising SEQ ID NO: 1. For instance, the peptide can comprise at least 10, 11, 12, 13, 14, 15, 16, 17, 18, 19, or 20 contiguous amino acids of SEQ ID NO: 1.

In some embodiments, the peptide comprises an amino acid sequence that has at least 80% identity to SEQ ID NO: 1. In some embodiments, the peptide comprises an amino acid sequence that has at least 80% identity to SEQ ID NO: 1, wherein the peptide is non-lytic and is capable of affecting the release of a polynucleotide from an endosome of a cell. The peptide comprising an amino acid sequence that has at least 80% identity to SEQ ID NO: 1, can have about 80%, about 85%, about 90%, or about 95% identity to the amino acid sequence of SEQ ID NO: 1. A peptide comprising an amino acid sequence that has at least 80% identity to SEQ ID NO: 1 may comprise one or more amino acids that have been conservatively substituted. For instance, one, two, three, four, five, or more than nine amino acids may be conservatively substituted as long as the resulting peptide functions substantially similar to a peptide comprising SEQ ID NO: 1.

In some embodiments, the polynucleotide is a siRNA, wherein the siRNA is at least about 80% (at least about 85%, about 90%, about 95%, about 98%, or about 99%) identical to SEQ ID NO: 4 or SEQ ID NO: 5.

In some embodiments, the peptide-polynucleotide complex comprises a ratio of peptide:polynucleotide that is more than about 50:1 and less than about 200:1. In some embodiments, the peptide-polynucleotide complex comprises a ratio of peptide:polynucleotide that is less than about 50:1. The molar ratio of the peptide to polynucleotide at which the peptide associates with a polynucleotide of the invention can and will vary depending on the peptide, the polynucleotide composition, or the size of the polynucleotide, and may be determined by one of skill in the art. In essence, a suitable molar ratio of a peptide of the invention to a polynucleotide of the invention may be a molar ratio wherein the peptide completely complexes the polynucleotide. For instance, a peptide may associate with a polynucleotide in a peptide to polynucleotide molar ratio of about 1:1, 10:1, 20:1, 30:1, 40:1, 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, or about 300:1 or more. In some embodiments, a peptide may associate with a polynucleotide in a peptide to polynucleotide molar ratio of about 20:1 to about 250:1. In some embodiments, a peptide may associate with a polynucleotide in a peptide to polynucleotide molar ratio of about 50:1 to about 200:1. In some embodiments, a peptide may associate with a polynucleotide in a peptide to polynucleotide molar ratio of about 75:1 to about 225:1. In some embodiments, a peptide may associate with a polynucleotide in a peptide to polynucleotide molar ratio of about 100:1 to about 200:1. In some embodiments, a peptide may associate with a polynucleotide in a peptide to polynucleotide molar ratio of about 125:1 to about 175:1.

Depending on the size and charge of the polynucleotide, the molar ratios can be larger. Thus, in other embodiments, a peptide may associate with a polynucleotide in a peptide to polynucleotide molar ratio of about 300:1, 400:1, 500:1, 600:1, 700:1, 800:1, 900:1, 1000:1, 1500:1, 2000:1, 2500:1, 3000:1, or more. In some embodiments, the peptide-polynucleotide complex comprises a ratio of peptide:polynucleotide that is more than about 300:1 and less than about 1000:1. In some embodiments, the peptide-polynucleotide complex comprises a ratio of peptide:polynucleotide that is more than about 1000:1 and less than about 3000:1.

In some aspects, disclosed herein is a method of delivering a polynucleotide to the cytoplasm of a cell, the method comprising:

contacting a cell with a composition, wherein the composition comprises:
- a peptide-polynucleotide complex, the peptide-polynucleotide complex comprising:
- a peptide;
- a polynucleotide; and
- hyaluronic acid;
- wherein the peptide is non-lytic and capable of affecting the release of a polynucleotide from an endosome of a cell; and
- wherein the peptide comprises an amino acid sequence with at least 80% identity to the amino acid sequence of SEQ ID NO: 1.

In some aspects, disclosed herein is a method of delivering a polynucleotide to the cytoplasm of a cell in a subject in need thereof, the method comprising:

contacting a cell in the subject with a composition, wherein the composition comprises:
- a peptide-polynucleotide complex, the peptide-polynucleotide complex comprising:
- a peptide;
- a polynucleotide; and
- hyaluronic acid;
- wherein the peptide is non-lytic and capable of affecting the release of a polynucleotide from an endosome of a cell; and
- wherein the peptide comprises an amino acid sequence with at least 80% identity to the amino acid sequence of SEQ ID NO: 1.

In some embodiments, the cell is a eukaryotic cell. In some embodiments, the cell is a mammalian cell. In some embodiments, the cell is a human cell. In some embodiments, the cell is a prokaryotic cell.

A peptide-polynucleotide complex may be incubated with hyaluronic acid for about 5, 10, 15, 20, 25, 30, 35, 40, 45, 50, 55, or about 60 minutes or more to allow the hyaluronic acid coat the peptide-polynucleotide complex or integrate into the peptide-polynucleotide complex. A peptide-polynucleotide complex may be incubated with hyaluronic acid for about 1, 2, 3, 4, 5, 10, 12, 18, or 24 hours or more, to allow the hyaluronic acid coat the peptide-polynucleotide complex or integrate into the peptide-polynucleotide complex. In some embodiments, a peptide-polynucleotide complex may be incubated with hyaluronic acid for about 45 minutes. Shorter times could be used in some embodiments, for example, when using microfluidic devices.

In another aspect, a composition described herein may comprise an excipient. This composition may be useful in a variety of medical and non-medical applications. For example, pharmaceutical compositions may be useful in the delivery of an effective amount of a polynucleotide to a subject in need thereof.

In certain embodiments, the polynucleotide is DNA or RNA. In certain embodiments, the RNA is RNAi, dsRNA, siRNA, shRNA, miRNA, or antisense RNA. In certain embodiments, the compositions comprise one or more additional active compounds. In certain embodiments, the composition further comprises an agent. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired.

General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy (Polyethylene glycol)-1000], 1,2-Distearoyl-sn-glycero-3-Phosphoethanolamine-N-[Methoxy (Polyethylene glycol)-2000], and 1,2-Distearoyl-sn-glycero-3-Phosphoethanolamine-N-[Methoxy (Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be an injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, c) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) from the composition only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The composition is admixed with an excipient and any needed preservatives or buffers as may be required. Ophthalmic formulation, ear drops, and eye drops are also contemplated as being within the scope of this invention.

The ointments, pastes, creams, and gels may contain excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compositions in a proper medium. Absorption enhancers can also be used to increase the flux of the compound across the skin. The rate can be controlled by either providing a rate controlling membrane or by dispersing the particles in a polymer matrix or gel.

In some aspects, disclosed herein is a method of treating or preventing a disease or disorder in a subject in need thereof, the method comprising:

- administering to the subject a therapeutically effective amount of a composition, wherein the composition comprises:
  - a peptide-polynucleotide complex, the peptide-polynucleotide complex comprising:
    - a peptide;
    - a polynucleotide; and
    - hyaluronic acid;
    - wherein the peptide is non-lytic and capable of affecting the release of a polynucleotide from an endosome of a cell; and
    - wherein the peptide comprises an amino acid sequence with at least 80% identity to the amino acid sequence of SEQ ID NO: 1.

In some aspects, disclosed herein is a method of treating or preventing an inflammatory disorder in a subject in need thereof, the method comprising:

- administering to the subject a therapeutically effective amount of a composition, wherein the composition comprises:
  - a peptide-polynucleotide complex, the peptide-polynucleotide complex comprising:
    - a peptide;
    - a polynucleotide; and
    - hyaluronic acid;
    - wherein the peptide is non-lytic and capable of affecting the release of a polynucleotide from an endosome of a cell; and
    - wherein the peptide comprises an amino acid sequence with at least 80% identity to the amino acid sequence of SEQ ID NO: 1.

In some aspects, disclosed herein is a method of treating or preventing osteoarthritis in a subject in need thereof, the method comprising:

- administering to the subject a therapeutically effective amount of a composition, wherein the composition comprises:

a peptide-polynucleotide complex, the peptide-polynucleotide complex comprising:
a peptide;
a polynucleotide; and
hyaluronic acid;
wherein the peptide is non-lytic and capable of affecting the release of a polynucleotide from an endosome of a cell; and
wherein the peptide comprises an amino acid sequence with at least 80% identity to the amino acid sequence of SEQ ID NO: 1.

In some aspects, disclosed herein is a method of treating or preventing an aortic abdominal aneurysm in a subject in need thereof, the method comprising:

administering to the subject a therapeutically effective amount of a composition, wherein the composition comprises:
a peptide-polynucleotide complex, the peptide-polynucleotide complex comprising:
a peptide;
a polynucleotide; and
hyaluronic acid;
wherein the peptide is non-lytic and capable of affecting the release of a polynucleotide from an endosome of a cell; and
wherein the peptide comprises an amino acid sequence with at least 80% identity to the amino acid sequence of SEQ ID NO: 1.

In some embodiments, the peptide comprises a variant of SEQ ID NO: 1, wherein the variant comprises at least 10 contiguous amino acids of SEQ ID NO: 1. In some embodiments, the peptide comprises a variant of SEQ ID NO: 1, wherein the variant comprises at least 10 contiguous amino acids of SEQ ID NO: 1 and functions substantially similar to a peptide comprising SEQ ID NO: 1. For instance, the peptide can comprise at least 10, 11, 12, 13, 14, 15, 16, 17, 18, 19, or 20 contiguous amino acids of SEQ ID NO: 1.

In some embodiments, the polynucleotide is a DNA. In some embodiments, the polynucleotide is WNT16 DNA. In some embodiments, the WNT16 DNA comprises the sequence of SEQ ID NO: 2, or a polynucleotide sequence having at or greater than about 80%, about 85%, about 90%, about 95%, or about 98% homology with SEQ ID NO: 2, or a polynucleotide comprising a portion of SEQ ID NO: 2. In some embodiments, the WNT16 DNA encodes the polypeptide sequence of SEQ ID NO: 3.

In some embodiments, the polynucleotide is an mRNA. In some embodiments, the polynucleotide is a WNT16 mRNA. In some embodiments, the polynucleotide is a mRNA encoded by the WNT16 DNA (SEQ ID NO: 2) described above. Accordingly, in some embodiments, the polynucleotide is a mRNA encoded by SEQ ID NO: 2, or encoded by a polynucleotide sequence having at or greater than about 80%, about 85%, about 90%, about 95%, or about 98% homology with SEQ ID NO: 2, or encoded by a polynucleotide comprising a portion of SEQ ID NO: 2. In some embodiments, the polynucleotide is a siRNA, wherein the siRNA is at least about 80% (at least about 85%, about 90%, about 95%, about 98%, or about 99%) identical to SEQ ID NO: 4 or SEQ ID NO: 5.

In another aspect, provided are methods of using the compositions disclosed herein, e.g., for the treatment of a disease, disorder or condition from which a subject suffers. It is contemplated that compositions will be useful in the treatment of a variety of diseases, disorders, or conditions, especially a system for delivering agents useful in the treatment of that particular disease, disorder, or condition. "Disease." "disorder," and "condition" are used interchangeably herein. In certain embodiments, the disease, disorder or condition from which a subject suffers is caused by an abnormality in a gene or chromosome of the subject.

For example, in one embodiment, provided is a method of treating disease, disorder, or condition from which a subject suffers, comprising administering to a subject in need thereof an effective amount of a composition disclosed herein. Exemplary disease, disorder, or conditions contemplated include, but are not limited to, aortic abdominal aneurysms, cardiovascular diseases, proliferative disorders, inflammatory disorders, autoimmune disorders, cancers, atherosclerosis, kidney diseases, lung diseases, infectious diseases, orthopedic diseases, musculoskeletal diseases, and ocular diseases.

In some embodiments, the cardiovascular disease is atherosclerosis. In some embodiments, the cardiovascular disease is myocardial infarction (heart attack). In some embodiments, the cardiovascular disease is stroke.

In certain embodiments, the condition is a proliferative disorder and, in certain embodiments, the composition further includes an anti-cancer agent. Exemplary proliferative diseases include, but are not limited to, tumors, benign neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goserelin and leuprolide), anti-androgens (e.g. flutamide and bicalutamide), photodynamic therapies (e.g. verteporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel. Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D. dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (Astra- Zeneca), BEZ235 (Novartis), BGT226 (Norvartis), XL765 (Sanofi Aventis), PF-4691502 (Pfizer), GDC0980 (Genetech), SF1126 (Semafoc) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

In certain embodiments, the condition is an inflammatory disorder and, in certain embodiments, the composition further includes an anti-inflammatory agent. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenia purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious anemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

The composition may be administered in such amounts, time, and route deemed necessary in order to achieve the desired result. The exact amount of the composition will vary from subject to subject, depending on the species, age, and general condition of the subject, the severity of the infection, the particular composition, its mode of administration, its mode of activity, and the like. The composition is preferably formulated in dosage unit form for case of administration and uniformity of dosage. It will be understood, however, that the total daily usage of the composition will be decided by the attending physician within the scope of sound medical judgment. The specific therapeutically effective dose level for any particular subject will depend upon a variety of factors including the disorder being treated and the severity of the disorder; the activity of the composition employed; the specific composition employed; the age, body weight, general health, sex and diet of the patient; the time of administration, route of administration, and rate of excretion of the specific composition employed; the duration of the treatment; drugs used in combination or coincidental with the specific composition employed; and like factors well known in the medical arts.

The composition may be administered by any route. In some embodiments, the composition is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the composition (e.g., its stability in the environment of the gastrointestinal tract), the condition of the subject (e.g., whether the subject is able to tolerate oral administration), etc.

The exact amount of a composition required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Kits

Another aspect of the invention encompasses a kit for preparing a peptide-polynucleotide complex. In some embodiments, the kit comprises a first composition comprising a peptide, a second composition comprises a polynucleotide, and a third composition comprising hyaluronic acid (HA). By following directions provided by the kit, a user of the kit may mix the composition comprising a peptide and a composition comprising a polynucleotide to form a peptide-polynucleotide complex, followed by incubation with hyaluronic acid. The directions of the kit may include instructions to mix the peptide and polynucleotide at a suitable ratio. Suitable ratios are described above. The kit may also include suitable buffers, water, or cross-linking reagents.

EXAMPLES

The following examples are set forth below to illustrate the compositions, nanoparticles, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Analysis of Hyaluronan-Coated p5RHH-siRNA Nanoparticles

In this example, novel siRNA peptide nanoparticles were formulated with a peptide based on modifications of the cationic amphipathic peptide melittin that is a component of bee venom. When the siRNA is combined with the peptide, the peptide condenses the siRNA into a nanoparticle. This nanoparticle was then combined with hyaluronic acid to generate a transfective 20-40 nm particle. Systemic delivery of siRNA or any nucleotide (e.g., mRNA, DNA, etc.) has been the goal of many labs and companies for two decades since the discovery of RNA interference. The nanoparticles herein show both unexpected physical properties and provide surprisingly potent nanoparticles.

After a selected time following mixing of the polynucleotide and the peptide (about 10-40 minutes), hyaluronic acid (HA) is added to the nanoparticle. The HA is a substitute for a more standard albumin coating. The substitution of albumin with hyaluronic acid yields a smaller and more homogeneous preparation of p5RHH-siRNA nanoparticles. Thus, these unexpected and unpredictable qualities of the resulting nanoparticles are highly desirable for improved transfection of cells for the delivery of polynucleotides.

Atomic Force Microscopy 0.2 mg/ml Hialuronan of 7.38*105 Da average molecular weight (Lifecore, HA700k-1, lot 025781) was used to coat 50 μM p5RHH+0.5 μM Cy3 labeled siRNA NP (incubated @ 37 C for 40 minutes as per protocol). NP were deposited for 3 minutes on a freshly cleaved mica, and then rinsed with DI water and dried with nitrogen. Images were taken using a MFP-3D atomic-force microscope (Asylum Research, SantaBarbara, CA) and PFP-FMR-50 (Nanosensor, Neuchatel, Switzerland) silicon tips with nominal tip radii of 10 and 7 nm, respectively. The cantilever had a typical spring constant and resonance frequency of 2 nN/nm and 70 kHz, respectively. It was driven at 60-70 kHz in alternating current mode and at a scan rate of 0.5 Hz, and images were acquired at 512× 512 pixel resolution.

Fluorescence Microscopy 10,000 NRK52E cells in a 4-well chambered slide were incubated with 10 μL of p5RHH/Cy3-siRNA NP (formulated as above for AFM images). Nuclei staining was performed with Vectashield mounting media (H-1200). Images were taken after 24 h using a 40× objective with an Olympus FV1200 Spectral Inverted Laser Scanning Confocal Microscope.

Preparation of Peptide/siRNA Nanoassemblies and Analysis

Melittin derivatives were synthesized by Genscript (Piscataway, NJ), dissolved at 10 mM in RNAse/DNAse free water (Sigma, St. Louis, MO) and stored in 4 μl aliquots at −80° C. before use. p5RHH/siRNA transfection complexes were prepared by diluting p5RHH 1:200 in phosphate buffered saline (PBS, Sigma), vortexed for 30 seconds followed by addition of the appropriate amount of siRNA (stock concentration of 10 μM in 1× siRNA buffer (Thermo Scientific, Waltham, MA)) and incubated for 40 minutes at 37° C. with shaking in an Eppendorf Thermomixer R. Resulting nanoparticles were analyzed for siRNA incorporation by resolution on a 12% polyacrylamide gel followed by ethidium bromide staining. Dynamic light scattering (DLS) and zeta potential measurements were performed on a Zeta Plus particle sizer (Brookhaven Instruments, Newton, MA). Serum stability analysis was performed by incubating freshly formed peptide/siRNA nanoparticles in 500 μg/ml human serum albumin (HSA, Sigma) overnight followed by DLS and zeta potential measurements. The sense sequence of the siRNA is GACGUAAACGGCCACAAGUUC (SEQ ID NO: 4). The antisense sequence of the siRNA is GAACUUGUGGCCGUUUACGUC) (SEQ ID NO: 5).

As shown in FIGS. 1A-1D, hyaluronan-coated p5RHH-siRNA nanoparticles (NP) were analyzed for their morphology and transfection. Atomic Force Microscopy images of Hialuronan coated p5RHH-siRNA NP show the uniform nanoparticles when using hyaluronic acid (hyaluronan) (FIGS. 1A, 1B). Images were obtained by superimposing the amplitude and height layers in Adobe Photoshop. NP heights of are given by the scale to the right. (C) Bright field images of NRK52E cells with superimposed Cy3 labeled (red) fluorescent NP indicating their intracellular uptake (FIG. 1C). The same image as shown in FIG. 1C was superimposed with Cy3 labeled fluorescent NP and DAPI (violet) fluorescence from NRK52E cells nuclei (FIG. 1D). As shown in FIG. 1, hyaluronan-coated p5RHH-siRNA nanoparticles yield an unexpectedly smaller and more homogeneous preparation of nanoparticles.

Figures 2A, 2B:
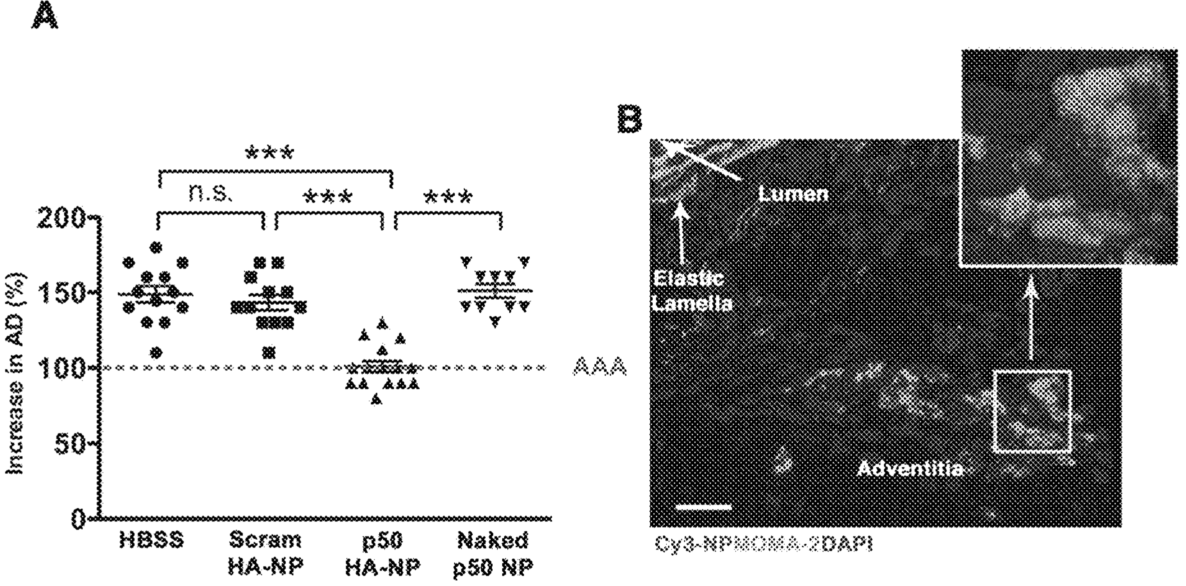
FIGS. 2A-2B show that treatment of mice with anti-NFkB siRNA nanoparticles coated with Hyaluronic Acid (HA) prevents Aortic Abdominal Aneurysm (AAA) formation. Mice were perfused in the abdominal portion of the aorta with elastase on day 0 to induce AAA. Mice were administered IV anti-NFkB p5RHH siRNA NP (p50-HA NP) or controls at 0.1 micromol of siRNA on day 5 and day 8.

Example 2. SiRNA Nanoparticles Coated with Hyaluronic Acid (HA) Prevent Aortic Abdominal Aneurysm (AAA) Formation As shown in FIGS. 2A-2B, treatment of mice with anti-NFkB siRNA nanoparticles coated with Hyaluronic Acid (HA) prevents Aortic Abdominal Aneurysm (AAA) formation. Mice were perfused in the abdominal portion of the aorta with elastase on day 0 to induce AAA. Mice were administered IV anti-NFkB p5RHH siRNA NP (p50-HA NP) or controls at 0.1 micromol of siRNA on day 5 and day 8. Any appropriate non-coding RNA (for example, siRNA) capable of disrupting expression of a nucleic acid sequence expressed in a cell can be used. The plot shows a 75% reduction in AAA incidence for p50 HA-NP compared to ineffective scrambled and naked NP (i.e., no enlargement in 75% of animals that do not exceed the red line for AAA) and significant mitigation of AAA, which is defined as an increase in aortic diameter (AD) of >100% at day 14 compared to pre-perfused AD on day 0 (FIG. 2A). Immunofluorescence confocal micrographs show colocalization of p50-siRNA (Cy3-NP: red) and macrophages (MOMA-2: green) as an orange color, indicating uptake by inflammatory cells in the adventitia that are responsible for aneurysm enlargement (FIG. 2B). This aneurysm suppressing dose of siRNA is 10-fold less than that used for experiments with other nanoparticles, indicating that the HA coating unexpectedly confers much greater efficacy to the system for gene expression knockdown and/or protein knockdown.

Example 3. Expression of WNT16 Via Peptide-mRNA Nanoparticle-Based Delivery Maintains Cartilage Homeostasis Osteoarthritis (OA) is a progressive disease that causes significant pain and suffering and for which there are limited medical treatment options. Although effective disease-modifying OA drugs (DMOADs) remain an unmet medical need, no therapeutics have successfully emerged in the clinic. The reasons for this failure are multifold, including the fact that primary OA is a complex, multifactorial disease with incompletely understood pathogenesis.

Much interest has recently focused on the role of inflammation and inflammatory cytokines in the pathogenesis of OA. It is posited that an imbalance between inflammatory (catabolic) and anabolic factors leads to cartilage degeneration, a hallmark of OA. Thus, blockade of catabolic cytokines such as TNF-α and IL-1β has gained attention as potential therapy. Indeed, intra-articular (IA) administration of IL-1 receptor antagonist (IL1-ra) exhibits disease-modifying effects in a rodent model of OA. However, in clinical studies, the administration of commercially available IL-1ra (Anakinra) had no therapeutic effect in established knee OA and so far only offers short-term improvement in pain and function if administered within the first month following knee injury (NCT00332254). Thus, novel approaches that promote and/or maintain joint homeostasis to mitigate OA progression are highly desirable.

The cartilage reparative process following joint injury is regulated by several pathways. The WNT signaling pathway has been implicated in the pathogenesis of OA. While activation of the canonical WNT/β-catenin pathway through WNT3A stimulates catabolic activities, WNT16 upregulation antagonizes excessive canonical WNT/β-catenin signaling to preserve cartilage homeostasis and promote repair. In this example, a peptidic nanoparticle (NP) structure was employed to overexpress WNT16 and its effect on cartilage extracellular matrix (ECM) production and cartilage homeostasis were examined.

Figures 3A, 3B:
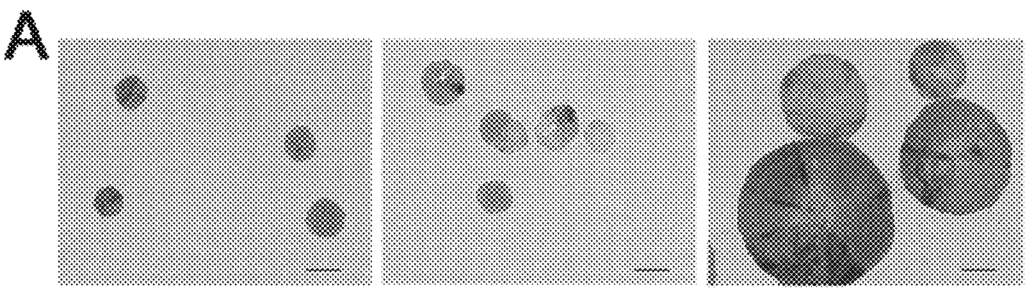
FIGS. 3A-3B show that HA-coated p5RHH-WNT16 mRNA NP was generated by mixing 1, 2 or 4 μg of mRNA with 10 μmol of p5RHH.

Results p5RHH-mRNA NP preparation and characterization. HA, a naturally occurring linear polysaccharide that is a major component of the ECM, is present in high concentration in the synovial fluid and hyaline cartilage and binds to the CD44 expressed on chondrocytes. HA is highly biocompatible and FDA-approved for the symptomatic treatment of osteoarthritis (OA), although the effect of free HA is modest, transient, and not-disease modifying. Here, the peptide-mRNA NP was functionalized with a HA coating to enhance chondrocyte targeting and uptake through CD44-HA interaction. The NP was prepared by mixing a set amount of p5RHH peptide (10 μmol) with increasing concentrations of WNT16 mRNA (~1,100 nt). The mixing of 10 μmol p5RHH with 1 μg of WNT16 mRNA (peptide:mRNA ratio 1:3,500) yielded a NP of ~70 nm after application of the HA coating, as measured by transmission electron microscopy (TEM, FIG. 3A), and a zeta potential of −30 mV by dynamic light scattering (DLS, FIG. 3B). Increasing the concentration of mRNA resulted in significantly increased particle diameter (>200 nm at mRNA concentration of 4 μg and peptide: mRNA ratio of 1:875, FIGS. 3A-B).

Figures 4A, 4B:
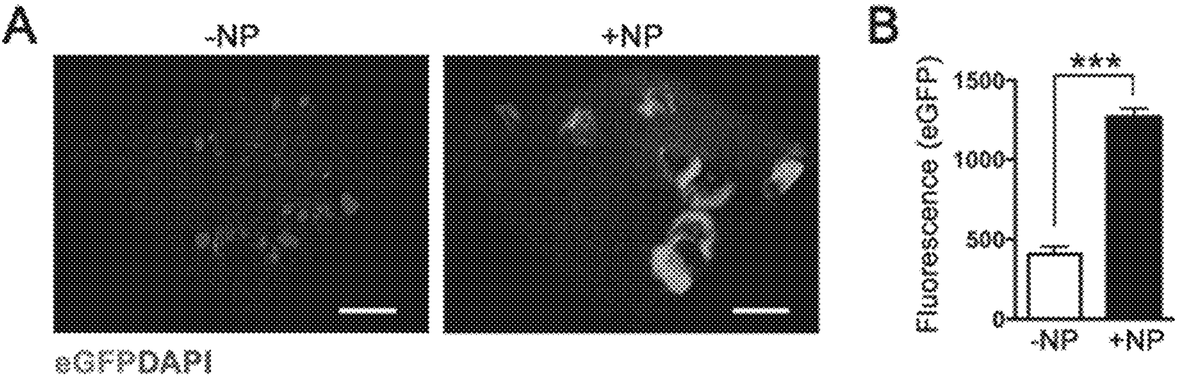
FIGS. 4A-4B show that HA-coated p5RHH-eGFP mRNA NP at 1 μg of mRNA and 10 μmol of p5RHH was incubated with 5 $mm^2$ cartilage discs derived from human knee joint. After 48 h, cartilage explants were washed, processed, and examined for eGFP expression in chondrocytes (FIG. 4A).

Delivery of eGFP mRNA in cartilage explants. To begin exploring the efficacy/efficiency of this nanoplatform in the delivery of mRNA to express anabolic factors, eGFP mRNA (~1,000 nt) was used for case of detection of the translated product. HA-coated p5RHH-eGFP mRNA NP was prepared by mixing 1 μg of eGFP mRNA with 10 μmol of p5RHH (peptide:mRNA ratio of 1:3,500) in a total volume of 100 μL of HBSS and incubated for 40 min at 37° C. HA (0.2 mg/mL) was used to coat the NP at 4° C. for 5 min following assembly of the NP. Prepared NP was diluted in culture medium and added to 5 $mm^2$ cartilage discs from human OA knee joints. The cartilage explants were harvested after 48 h in culture and examined for eGFP expression. Efficient cartilage expression of eGFP was observed with transfection of the NP (FIG. 4).

Figures 5A, 5B, 5C, 5D, 5E, 5F:
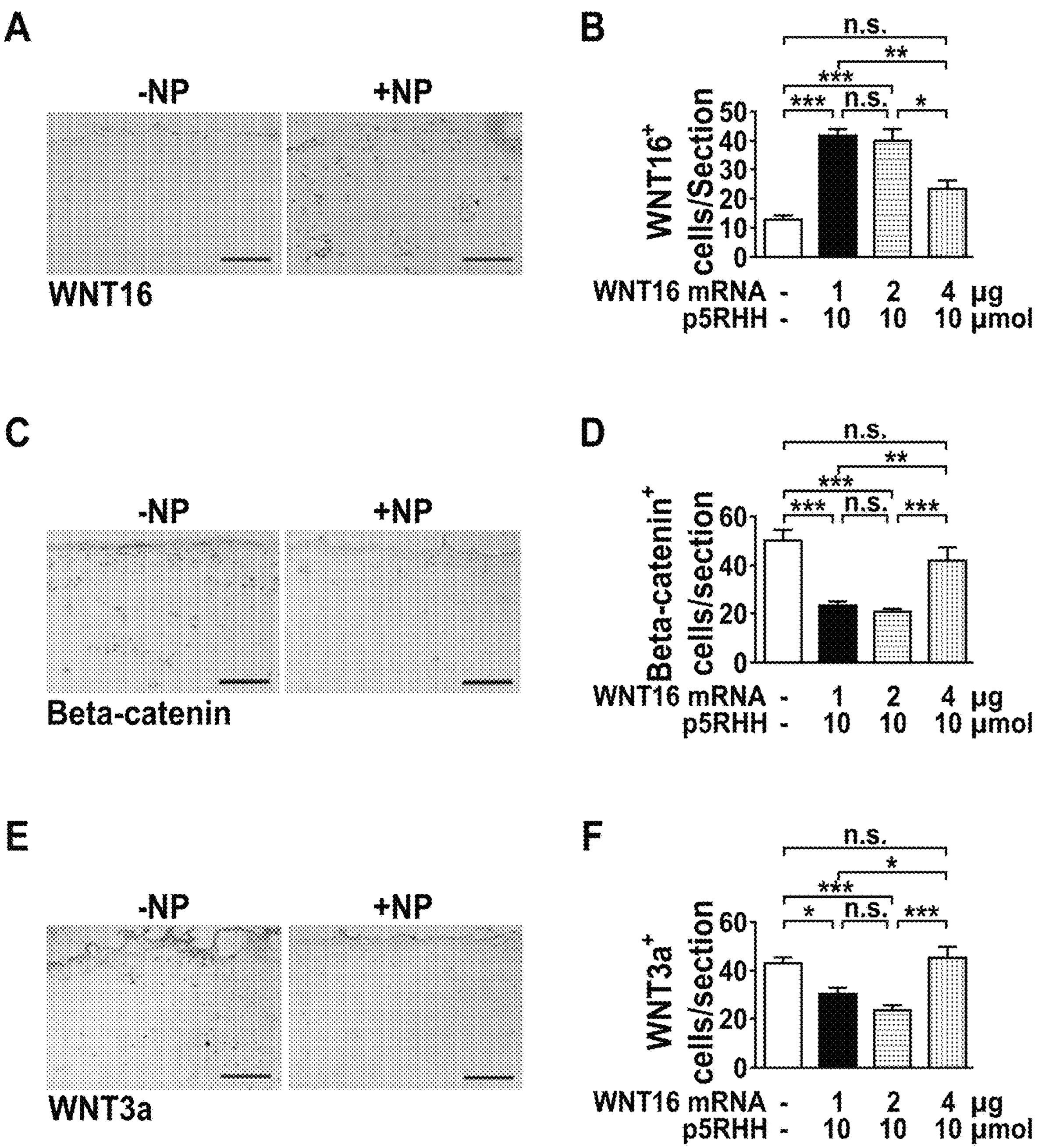
FIGS. 5A-5F show that HA-coated p5RHH-WNT16 mRNA NP generated at the indicated concentrations of mRNA and p5RHH was incubated with 5 $mm^2$ cartilage discs derived from human knee joint. After 48 h, cartilage explants were washed, processed, and examined for WNT16 (FIGS. 5A-5B), Beta-catenin (FIGS. 5C-5D) and WNT3a (FIGS. 5E-5F) expression. IHC photomicrographs were derived from cartilage discs transfected with 1 μg of peptide-mRNA NP. Scale bar=100 μm. The numbers of WNT16+, beta-catenin+, and WNT3a+ cells/cartilage section were enumerated. Data were derived from 6 to 8 cartilage sections, from 4-6 independent human cartilage explants. *P<0.05, P<0.01. *P<0.001, n.s. not significant.

Delivery of WNT16 mRNA in cartilage explants. The delivery of WNT16 mRNA was next tested. The purified WNT16 mRNA construct was produced commercially and contained the appropriate endcaps and poly-A tail. HA-coated p5RHH-WNT16 mRNA NP were prepared using 3 different concentrations of mRNA: 1 μg, 2 μg or 4 μg. The self-assembled NP was incubated with human cartilage explants for 48 h then examined for protein expression of WNT16, β-catenin and WNT3a. It was found that expression of WNT16 was significantly enhanced with the delivery of mRNA at 1 μg and 2 μg but not at 4 μg (FIGS. 5A-5B), because the size of the self-assembled NP at this concentration (4 μg) of mRNA is too big for efficient cartilage penetration (FIG. 3). Increased WNT16 expression was accompanied by decreased β-catenin (FIGS. 5C-5D) and WNT3a (FIGS. 5E-5F).

Figures 6A, 6B, 6C, 6D:
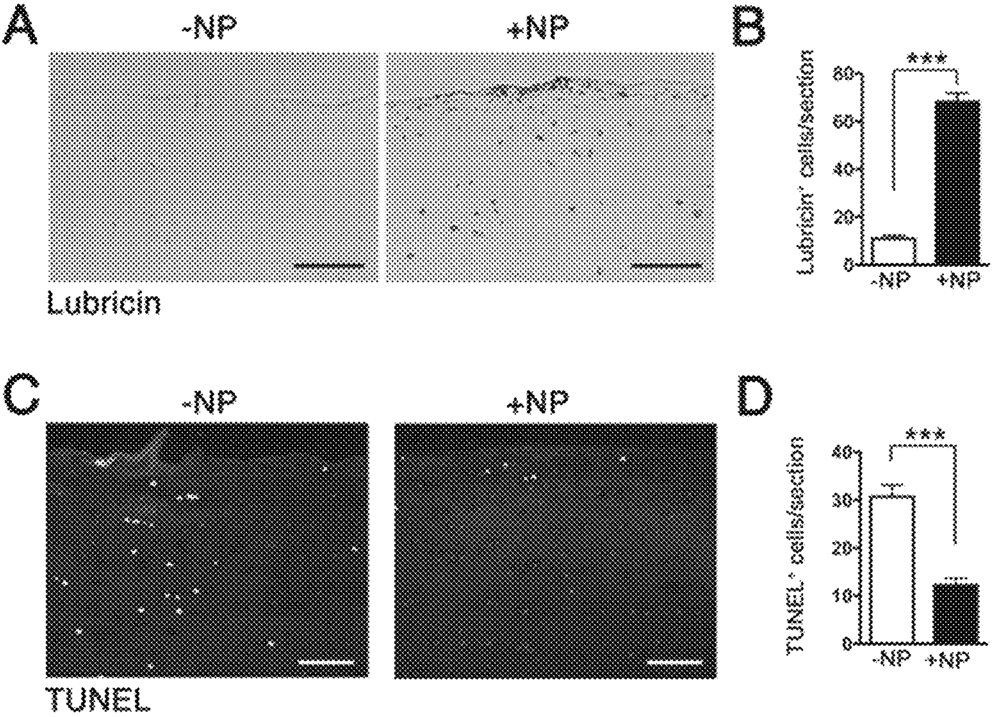
FIGS. 6A-6D show that HA-coated p5RHH-WNT16 mRNA NP generated at 1 μg of mRNA and 10 μmol of p5RHH was incubated with 5 $mm^2$ cartilage discs derived from human knee joint. After 48 h, cartilage explants were washed, processed, and examined for lubricin expression (FIGS. 6A-B6) and TUNEL+ cells (FIGS. 6C-6D). Scale bar=100 μm. The numbers of Lubricin+ and TUNEL+ cells/cartilage section were enumerated. Data were derived from 6 to 8 cartilage sections, from 4-6 independent human cartilage explants. ***P<0.001.

Effect of WNT16 overexpression on cartilage homeostasis. The expression of lubricin was next examined, an essential joint lubricant that protects against chondrocyte apoptosis and cartilage deterioration. It was observed that WNT16 mRNA delivery led to significant upregulation of lubricin-expressing cells and lubricin in the superficial layers of the cartilage explants (FIGS. 6A-6B), which in turn led to suppression of chondrocyte apoptosis, as evidenced by a decrease in the number of TUNEL+ cells (FIGS. 6C-6D).

The challenge of delivering nanotherapeutics to cartilage in effective doses in vivo is well known. Critical barriers include inefficient delivery to the chondrocytes residing in the avascular cartilage tissue and the dense ECM that excludes large particles from entering the deeper layers to deliver the therapeutic cargo. Employed herein is the amphipathic cationic peptide p5RHH that is a modified version of the natural peptide melittin, which rapidly forms a biocompatible and stable nanocomplex upon mixing of peptide and nucleotide components that deeply penetrates human cartilage. The complex protects the RNA from degradation and once taken up inside the cell, the peptide can facilitate endosomal escape and coordinated release of nucleic acid structures. Herein it is shown for the first time that p5RHH can also complex with mRNA structures (up to ~1,100 nt) to form stable NP of ~70 nm, small enough to penetrate cartilage for delivery and translation of the mRNA. The versatility of the platform to incorporate short and long nucleotide structures significantly broadens the range of clinical applications for this technology.

Approaches to osteoarthritis (OA) treatment have recently shifted toward anabolic pathways that promote cartilage repair and homeostasis. Fibroblast growth factors (FGFs) are important regulators of cartilage development and homeostasis. Intra-articular (IA) injection of FGF-18 in a rat meniscal tear model induces new cartilage formation. Sprifermin (AS902330), a recombinant form of human FGF-18 injected IA in patients with advanced or end-stage OA shows early promise; however, no significant change in symptom scores is seen at 2 years. Likewise, excessive (β-catenin-dependent) canonical WNT activation leads to cartilage breakdown and increases risk of OA. A small molecule inhibitor of the WNT pathway (SM04690) shows protective and regenerative effects in an OA animal model and has the potential on being disease modifying in knee OA; however, long-term effects are still unknown (ongoing trials NCT03727022). In this example, it was shown that overexpression of WNT16 suppresses canonical β-catenin/WNT3a signaling. The p5RHH platform, by its ability to accommodate of a wide range of oligonucleotide structures (siRNA, mRNA, and others) without the need for backbone or end-piece alterations enables the delivery of a "cocktail" of factors (anti-inflammatory and anabolic) that can control cartilage loss and maintain homeostasis, mitigating OA progression. This example examined WNT16 expression at 48 hours following in vitro transfection in cartilage explants. The nanocomplex IA was delivered in OA models to determine level and duration of expression as well as effects on cartilage homeostasis in vivo.

Materials and Methods

Preparation of sodium hyaluronic acid (HA)-coated p5RHH-mRNA NP. 10 mg sodium hyaluronic acid (Part #HAIM-1, Lifecore Biomedical) was dissolved in 1 ml HBSS with Ca++/Mg++ by sonification for 60 min and ultra-centrifuged at 90,000 g for 40 m. The supernatant was aliquoted and stored at −80° C. until use. p5RHH peptide (VLTTGLPALISWIRRRHRRHC (SEQ ID NO: 1), provided by Genscript) was dissolved at 10 mM in DNAse-, RNAse-, and protease-free sterile purified water (Cellgro) and stored in 10-μl aliquots at −80° C. until use.

The p5RHH-mRNA nNP was prepared as follows: 1 μg of Cy5-eGFP mRNA (TriLink Biotechnologies, San Diego) or 1, 2, or 4 μg of WNT16 mRNA (TriLink Biotechnologies, San Diego) in HBSS with Ca++/Mg++ were added to 10 μmol of p5RHH peptide (in a total volume of 100 μL), mixed well, and incubated at 37° C. for 40 min. After incubation, 5 μL of HA was added to the self-assembled NP and placed on ice for 5 min. This mixture was diluted into a total volume of 500 μL with culture medium for in vitro transfection. NP size was measured by transmission electron microscopy (TEM) and zeta potential by dynamic light scattering (DLS). To calculate the actual spherical volume of the NP from their "flattened" shape acquired during the TEM drying process, the formula for the volume of a right cylinder was used ($V=\pi r^2 h$, where V=volume, r=radius, and h (height) was assumed to be $1/5^{th}$ of their flattened diameter). The radius for a sphere of the same volume as the right cylinder was calculated from the formula $V=4/3\pi r^3$.

Human cartilage explant culture. Human cartilage explants were obtained from consented patients through a protocol approved by the Washington University in St. Louis Institutional Review Board (IRB) at time of total knee arthroplasty and all study participants provided written informed consent. The de-identified cartilage tissues were washed several times with HBSS containing antibiotics then incubated in DMEM/F12 (1:1) medium containing 10% FBS, penicillin/streptomycin (100 U/0.1 mg/mL), amphotericin B (0.25 μg/mL), and ciproflaxin (10 μg/mL) in a 6-well plate at 37° C. and 5% $CO_2$ for 2-3 days. The explants were then transferred to a 96-well plate and subsequently exposed to the aforementioned p5RHH-mRNA NP for 48 h. The excess NP was washed off after 48 h incubation. The cartilage explants were harvested and then embedded in Tissue-Tek Optimal Cutting Temperature (O.C.T.) compound (Sakura Finetek USA, Inc.) and sectioned for analysis.

TUNEL assay. The apoptotic assay was performed to identify DNA fragmentation associated with terminal deoxynucleotidyl transferase-mediated dUTP nick-end labeling (TUNEL). Detection of apoptotic cells was performed on non-fixed frozen cartilage sections using an in situ Cell Death Detection Kit (Cat: 11-684-795-910, Roche). In brief, the cartilage sections were rinsed with PBS, then permeabilized with 0.5% TWEEN-20/PBS for 15 min and blocked with 8% BSA solution. Freshly prepared TUNEL reaction mixture, according to the manufacturer's protocol, was applied to the sections for 1 h at 37° C., rinsed 3 to 5 times with PBS, and probed with COL2 antibody (1:200 dilution, generously provided by L. J. Sandell and M. F. Rai, Washington University, St. Louis) followed by TRITC-conjugated anti-rat secondary antibody (1:100 dilution, Cat #712-295-153, Jackson ImmunoResearch) and counterstained with DAPI (1:1,000 dilution, Vector Laboratories). The sections were mounted with VECTASHIELD mounting medium with DAPI (Cat: H-1200, Vector Laboratories). The TUNEL+ cells were enumerated across non-overlapped fields. Data represent 6-8 sections per cartilage, 4-6 patients per treatment.

Confocal microscopy. After incubation with eGFP mRNA NPs for 48 h, the cartilage explants were harvested and sectioned. Frozen sections (9 μm) were rinsed, fixed and covered with VECTASHIELD mounting medium with DAPI (1:1,000, Vector Laboratories) at room temperature. The images were acquired with ZEISS LSM 880 Confocal Laser Scanning Microscope and 15 to 20 cells per section and 3-4 sections were analyzed with software ZEN. The data was presented as the mean fluorescent intensity per cell.

Immunohistochemistry. Formalin-fixed, OCT-embedded 9 μm sections of human cartilage explants were probed with WNT16 (1:100 dilution, Cat #LS-A9629, LifeSpan Biosciences), WNT3A (1:100 dilution, Cat #OABF00803, Aviva Systems Biology), Lubricin (1:200 dilution, Cat #55463, MP Biomedicals) or β-catenin (1:100, Cat #ab16051, Abcam, Cambridge, United Kingdom) at room temperature for 1 h. After washing, the sections were incubated with the corresponding HRP-conjugated secondary antibodies for 1 h. Data presented was derived from 6 to 8 cartilage sections. The pattern was confirmed on 4-6 independent human cartilage explants.

Statistics. Comparisons between multiple groups (>3) were performed by one-way ANOVA followed by Bonferroni's correction for multiple comparisons was performed. Differences between experimental groups at a P value of <0.05 were considered significant.

The following abbreviations are used in this example.

DLS Dynamic Light Scattering
eGFP enhanced Green Fluorescent Protein
ECM Extracellular Matrix
FGF Fibroblast Growth Factor
mRNA messenger RNA
NP Nanoparticle
OA Osteoarthritis
SiRNA small interfering RNA
TEM Transmission Electron Microscopy
TUNEL Terminal deoxynucleotidyl transferase dUTP and nick labeling Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Sequences

```
(peptide sequence of peptide-polynucleotide
complex)
                                    SEQ ID NO: 1
VLTTGLPALISWIRRRHRRHC
```

```
(a sequence of WNT 16 DNA)
                                    SEQ ID NO: 2
ATGGACAGGGCGGCGCTCCTGGGACTGGCCCGCTTGTGCGCGCTGTGGG

CAGCCCTGCTCGTGCTGTTCCCCTACGGAGCCCAAGGAAACTGGATGTG

GTTGGGCATTGCCTCCTTCGGGGTTCCAGAGAAGCTGGGCTGCGCCAAT

TTGCCGCTGAACAGCCGCCAGAAGGAGCTGTGCAAGAGGAAACCGTACC
```

-continued

```
TGCTGCCGAGCATCCGAGAGGGCGCCCGGCTGGGCATTCAGGAGTGCGG

GAGCCAGTTCAGACACGAGAGATGGAACTGCATGATCACCGCCGCCGCC

ACTACCGCCCCGATGGGCGCCAGCCCCCTCTTTGGCTACGAGCTGAGCA

GCGGCACCAAAGAGACAGCATTTATTTATGCTGTGATGGCTGCAGGCCT

GGTGCATTCTGTGACCAGGTCATGCAGTGCAGGCAACATGACAGAGTGT

TCCTGTGACACCACCTTGCAGAACGGCGGCTCAGCAAGTGAAGGCTGGC

ACTGGGGGGGCTGCTCCGATGATGTCCAGTATGGCATGTGGTTCAGCAG

AAAGTTCCTAGATTTCCCCATCGGAAACACCACGGGCAAAGAAAACAAA

GTACTATTAGCAATGAACCTACATAACAATGAAGCTGGAAGGCAGGCTG

TCGCCAAGTTGATGTCAGTAGACTGCCGCTGCCACGGAGTTTCCGGCTC

CTGTGCTGTGAAAACATGCTGGAAAACCATGTCTTCTTTTGAAAAGATT

GGCCATTTGTTGAAGGATAAATATGAAAACAGTATCCAGATATCAGACA

AAACAAAGAGGAAAATGCGCAGGAGAGAAAAAGATCAGAGGAAAATACC

AATCCATAAGGATGATCTGCTCTATGTTAATAAGTCTCCCAACTACTGT

GTAGAAGATAAGAAACTGGGAATCCCAGGGACACAAGGCAGAGAATGCA

ACCGTACATCAGAGGGTGCAGATGGCTGCAACCTCCTCTGCTGTGGCCG

AGGTTACAACACCCATGTGGTCAGGCACGTGGAGAGGTGTGAGTGTAAG

TTCATCTGGTGCTGCTATGTCCGTTGCAGGAGGTGTGAAAGCATGACTG

ATGTCCACACTTGCAAGTAA
```

```
(a polypeptide of WNT16)
                                    SEQ ID NO: 3
MDRAALLGLARLCALWAALLVLFPYGAQGNWMWLGIASFGVPEKLGCAN

LPLNSRQKELCKRKPYLLPSIREGARLGIQECGSQFRHERWNCMITAAA

TTAPMGASPLFGYELSSGTKETAFIYAVMAAGLVHSVTRSCSAGNMTEC

SCDTTLQNGGSASEGWHWGGCSDDVQYGMWFSRKFLDFPIGNTTGKENK

VLLAMNLHNNEAGRQAVAKLMSVDCRCHGVSGSCAVKTCWKTMSSFEKI

GHLLKDKYENSIQISDKTKRKMRRREKDQRKIPIHKDDLLYVNKSPNYC

VEDKKLGIPGTQGRECNRTSEGADGCNLLCCGRGYNTHVVRHVERCECK

FIWCCYVRCRRCESMTDVHTCK
```

```
(siRNA sense sequence)
                                    SEQ ID NO: 4
GACGUAAACGGCCACAAGUUC
```

```
                                    SEQ ID NO: 5
(antisense sequence of siRNA)
GAACUUGUGGCCGUUUACGUC
```

We claim:

1. A pharmaceutical composition comprising a peptide-polynucleotide complex, the peptide-polynucleotide complex comprising:

a peptide;

a polynucleotide; and hyaluronic acid;

wherein the peptide comprises an amino acid sequence which is at least 95% identical to the full-length amino acid sequence of SEQ ID NO: 1; and wherein the peptide comprises one conservative amino acid substitution.

2. The composition of claim 1, wherein the peptide-polynucleotide complex is about 10 nm to about 150 nm in diameter.

3. The composition of claim 2, wherein the peptide-polynucleotide complex is about 10 nm to about 50 nm in diameter.

4. The composition of claim 1, wherein the hyaluronic acid coats the peptide-polynucleotide complex.

5. The composition of claim 1, wherein the hyaluronic acid is integrated into the peptide-polynucleotide complex.

6. The composition of claim 1, wherein the polynucleotide is an RNA.

7. The composition of claim 1, wherein the polynucleotide is an mRNA.

8. The composition of claim 1, wherein the polynucleotide is a non-coding RNA capable of regulating or inhibiting the expression of a nucleic acid sequence.

9. The composition of claim 8, wherein the non-coding RNA is an siRNA.

10. The composition of claim 8, wherein the non-coding RNA is an miRNA.

11. The composition of claim 1, wherein the peptide is cationic.

12. The composition of claim 1, wherein the peptide-polynucleotide complex comprises a ratio of peptide:polynucleotide that is more than about 50:1 and less than about 200:1.

13. A method of delivering a polynucleotide to the cytoplasm of a cell, the method comprising: contacting a cell with the composition of claim 1.

14. A method of treating osteoarthritis in a subject, comprising administering to the subject a therapeutically effective amount of the composition of claim 1.

* * * * *

SEQUENCE LISTING

```
Sequence total quantity: 5
SEQ ID NO: 1            moltype = AA  length = 21
FEATURE                 Location/Qualifiers
REGION                  1..21
                        note = Synthetic construct
```

```
source                  1..21
                        mol_type = protein
                        organism = synthetic construct
SEQUENCE: 1
VLTTGLPALI SWIRRRHRRH C                                            21

SEQ ID NO: 2            moltype = DNA  length = 1098
FEATURE                 Location/Qualifiers
misc_feature            1..1098
                        note = Synthetic construct
source                  1..1098
                        mol_type = other DNA
                        organism = synthetic construct
SEQUENCE: 2
atggacaggg cggcgctcct gggactggcc cgcttgtgcg cgctgtgggc agccctgctc  60
gtgctgttcc cctacggagc ccaaggaaac tggatgtggt tgggcattgc ctccttcggg  120
gttccagaga agctgggctg cgccaatttg ccgctgaaca gccgccagaa ggagctgtgc  180
aagaggaaac cgtacctgct gccgagcatc cgagagggcg cccggctggg cattcaggag  240
tgcgggagcc agttcagaca cgagagatgg aactgcatga tcaccgccgc cgccactacc  300
gccccgatgg gcgccagccc cctctttggc tacgagctga gcagcggcac caaagagaca  360
gcatttattt atgctgtgat ggctgcaggc ctggtgcatt ctgtgaccag gtcatgcagt  420
gcaggcaaca tgacagagtg ttcctgtgac accaccttgc agaacggcgg ctcagcaagt  480
gaaggctggc actggggggg ctgctccgat gatgtccagt atggcatgtg gttcagcaga  540
aagttcctag atttccccat cggaaacacc acgggcaaag aaaacaaagt actattagca  600
atgaacctac ataacaatga agctggaagg caggctgtcg ccaagttgat gtcagtagac  660
tgccgctgcc acggagtttc cggctcctgt gctgtgaaaa catgctggaa aaccatgtct  720
tcttttgaaa agattggcca tttgttgaag gataaatatg aaaacagtat ccagatatca  780
gacaaaacaa agaggaaaat gcgcaggaga gaaaaagatc agaggaaaat accaatccat  840
aaggatgatc tgctctatgt taataagtct cccaactact gtgtagaaga taagaaactg  900
ggaatcccag ggacacaagg cagagaatgc aaccgtacat cagagggtgc agatggctgc  960
aacctcctct gctgtggccg aggttacaac acccatgtgg tcaggcacgt ggagaggtgt  1020
gagtgtaagt tcatctggtg ctgctatgtc cgttgcagga ggtgtgaaag catgactgat  1080
gtccacactt gcaagtaa                                                1098

SEQ ID NO: 3            moltype = AA  length = 365
FEATURE                 Location/Qualifiers
REGION                  1..365
                        note = Synthetic construct
source                  1..365
                        mol_type = protein
                        organism = synthetic construct
SEQUENCE: 3
MDRAALLGLA RLCALWAALL VLFPYGAQGN WMWLGIASFG VPEKLGCANL PLNSRQKELC  60
KRKPYLLPSI REGARLGIQE CGSQFRHERW NCMITAAATT APMGASPLFG YELSSGTKET  120
AFIYAVMAAG LVHSVTRSCS AGNMTECSCD TTLQNGGSAS EGWHWGGCSD DVQYGMWFSR  180
KFLDFPIGNT TGKENKVLLA MNLHNNEAGR QAVAKLMSVD CRCHGVSGSC AVKTCWKTMS  240
SFEKIGHLLK DKYENSIQIS DKTKRKMRRR EKDQRKIPIH KDDLLYVNKS PNYCVEDKKL  300
GIPGTQGREC NRTSEGADGC NLLCCGRGYN THVVRHVERC ECKFIWCCYV RCRRCESMTD  360
VHTCK                                                              365

SEQ ID NO: 4            moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 4
gacgtaaacg gccacaagtt c                                            21

SEQ ID NO: 5            moltype = RNA  length = 21
FEATURE                 Location/Qualifiers
misc_feature            1..21
                        note = Synthetic construct
source                  1..21
                        mol_type = other RNA
                        organism = synthetic construct
SEQUENCE: 5
gaacttgtgg ccgtttacgt c                                            21
```